United States Patent [19]

Prakash et al.

[11] Patent Number: 5,856,584
[45] Date of Patent: Jan. 5, 1999

[54] PREPARATION OF 3,3-DIMETHYLBUTYRALDEHYDE BY OXIDATION OF 3, 3-DIMETHYLBUTANOL

[75] Inventors: Indra Prakash; David J. Ager, both of Hoffman Estates, Ill.; Alan R. Katritzky, Gainesville, Fla.

[73] Assignee: The Nutrasweet Company, Chicago, Ill.

[21] Appl. No.: 907,048

[22] Filed: Aug. 6, 1997

[51] Int. Cl.⁶ .................................................. C07C 45/47
[52] U.S. Cl. .......................... 568/449; 568/450; 568/840
[58] Field of Search ................................. 568/449, 450, 568/840

[56] References Cited

FOREIGN PATENT DOCUMENTS 0374952  6/1990  European Pat. Off. ...... C07D 493/08
0391652 10/1990  European Pat. Off. ...... C07D 493/08

OTHER PUBLICATIONS

Journal of Organic Chemistry, vol. 54, p. 570 (1989), C.K. Cheung, et al.
Journal of the American Chemical Society, vol. 103, p. 4473 (1981), K.B. Wiberg, et al.
Tetrahedron Letters, (1972), p. 257, M.Y. Sheikh et al.
Journal of Organic Chemistry, vol. 52, p. 2559 (1987), P.L. Anelli et al.
Organic Synthesis, vol. 69, p. 212 (1990), P.L. Anelli et al.
Journal of Organic Chemistry, vol. 61, p. 7452 (1996), J. Einhorn et al.
Journal of Organic Chemistry, vol. 61, p. 2918 (1996), N.S. Wilson et al.
Harrison et al: Compendium of Organic Synthetic Methods, pp. 137–143, 1971.

*Primary Examiner*—Gary Geist
*Assistant Examiner*—Sreeni Padmanabhan
*Attorney, Agent, or Firm*—Fitzparick, Cella Harper & Scinto

[57] ABSTRACT

This invention provides a method for preparing 3,3-dimethylbutyraldehyde from 3,3-dimethylbutanol using an oxidizing component. In one embodiment, 3,3-dimethylbutanol is oxidized to 3,3-dimethylbutyraldehyde in the vapor phase by contacting it with an oxidizing metal oxide compound. In another embodiment, the oxidation of 3,3-dimethylbutanol is carried out by treating it with 2,2,6,6-tetramethyl-1-piperidinyloxy, free radical and an oxidizing agent in a solvent to produce 3,3-dimethylbutyraldehyde. The method of this invention provides a commercially practicable means of preparing 3,3-dimethylbutyraldehyde.

17 Claims, No Drawings

PREPARATION OF 3,3-DIMETHYLBUTYRALDEHYDE BY OXIDATION OF 3,3-DIMETHYLBUTANOL

BACKGROUND OF THE INVENTION

1. Field of the Invention

This invention relates to a method for preparing 3,3-dimethylbutyraldehyde by oxidation of 3,3-dimethylbutanol. In a first embodiment, 3,3-dimethylbutanol is contacted with a metal oxide. In a second embodiment, 3,3-dimethylbutanol is treated with 2,2,6,6-tetramethyl-1-piperidinyloxy, free radical and an oxidizing agent.

2. Related Background Art

Several methods are known for the preparation of 3,3-dimethylbutyraldehyde by oxidation of 3,3-dimethylbutanol.

In EP 0391652 and EP 0374952, 3,3-dimethylbutyraldehyde is produced by oxidation of 3,3-dimethylbutanol with oxalyl chloride, dimethyl sulfoxide, and triethylamine in a dichloromethane solution. This procedure is the well known Swern oxidation, which produces extremely malodorous dimethyl sulfide as a byproduct. Use of this procedure on a commercial scale requires costly and inefficient measures to prevent release of objectionable quantities of dimethyl sulfide. This is a major disadvantage.

A similar procedure is reported in Cheung, C. K. et al., Journal of Organic Chemistry, Vol. 54, p. 570 (1989). This reference describes mixing 3,3-dimethylbutanol, dimethyl sulfoxide, trifluoroacetic acid, pyridine, and dicyclohexylcarbodiimide in benzene to produce 3,3-dimethylbutyraldehyde. The major disadvantage of this procedure is that, like the Swern oxidation, it produces dimethyl sulfide as a byproduct. Another disadvantage of the procedure is that isolation of the product requires removal of the byproduct dicyclohexylurea and distillation to purify the product.

Oxidation of 3,3-dimethylbutanol has also been carried out using pyridinium chlorochromate, as described in Wiberg, K. B., et al., Journal of the American Chemical Society, Vol. 103, p. 4473 (1981). This method has the disadvantage of using an extremely toxic chromium salt which must be completely removed from the product. In addition, use of this method necessitates expensive disposal of chromium-containing waste streams from the reaction.

It is also possible to oxidize 3,3-dimethylbutanol with a catalytic amount of $PdCl_2(CH_3CN)_2$, together with triphenylphosphine and 2-bromomesitylene in N,N-dimethylformamide and water. Einhorn, J., et al., Journal of Organic Chemistry, Vol. 61, p. 2918 (1996). This procedure, however, requires a relatively expensive catalyst.

General methods are known for the oxidation of alcohols to aldehydes with either copper(II) oxide or 2,2,6,6-tetramethyl-1-piperidinyloxy, free radical.

The vapor-phase oxidation of alcohols by copper(II) oxide is described in Sheikh, M. Y., et al., Tetrahedron Letters, 1972, p. 257. Although oxidation of a number of primary alcohols to the corresponding aldehydes is described, none of these alcohols has a branched carbon skeleton as does 3,3-dimethylbutanol. No suggestion is made that the procedure is applicable to oxidation of such compounds.

Oxidation of primary and benzylic alcohols by hypochlorite in solution, catalyzed by 4-methoxy-2,2,6,6-tetramethyl-1-piperidinyloxy, free radical is described in Anelli, P. L., et al., Journal of Organic Chemistry, Vol. 52, p. 2559 (1987); Anelli, P. L., et al., Organic Synthesis, Vol. 69, p. 212 (1990). These references also mention use of 2,2,6,6-tetramethyl-1-piperidinyloxy, free radical, but do not suggest that either of these oxidizing agents is suitable for oxidation of 3,3-dimethylbutanol.

Oxidation of alcohols with N-chlorosuccinimide, catalyzed by 2,2,6,6-tetramethyl-1-piperidinyloxy, free radical is reported in Einhorn, J., et al., Journal of Organic Chemistry, Vol. 61, p. 7452 (1996). No suggestion is made that this procedure is applicable to oxidation of 3,3-dimethylbutanol.

3,3-Dimethylbutyraldehyde is an intermediate that is useful in the preparation of the sweetener N-[N-(3,3-dimethylbutyl)-L-α-aspartyl]-L-phenylalanine disclosed in U.S. Pat. No. 5,480,668 and U.S. Pat. No. 5,510,508. Accordingly, a method for preparing that intermediate which is both economical and specific is highly desired.

SUMMARY OF THE INVENTION

This invention is directed to a method for preparing 3,3-dimethylbutyraldehyde from 3,3-dimethylbutanol using an oxidizing component described in more particularity below. In one embodiment, 3,3-dimethylbutanol is oxidized to 3,3-dimethylbutyraldehyde in the vapor phase by contacting it with an oxidizing metal oxide compound. In another embodiment, the oxidation of 3,3-dimethylbutanol is carried out by treating it with 2,2,6,6-tetramethyl-1-piperidinyloxy, free radical and an oxidizing agent in a solvent to produce 3,3-dimethylbutyraldehyde. The method of this invention provides a commercially practicable means of preparing 3,3-dimethylbutyraldehyde.

DETAILED DESCRIPTION OF THE INVENTION

In a first embodiment of this invention, oxidation of 3,3-dimethylbutanol to 3,3-dimethylbutyraldehyde is carried out by passing vaporized starting material in an inert carrier gas over an oxidizing metal oxide. The mixture of carrier gas and starting material is typically passed through a metal column packed with the oxidizing metal oxide. The flow rate, reaction temperature, residence time, column length and diameter, concentration of starting material, and column packing material, are interdependent and may be readily determined by one of ordinary skill in the art without undue experimentation.

The reaction temperature is generally set to ensure oxidation while substantially precluding over-oxidation. Suitable reaction temperatures for this method are typically in the range from about 250° C. to about 350° C. Preferably, the reaction is carried out at about 300° C.

Generally, a carrier gas is employed to facilitate transport of the 3,3-dimethylbutanol over an oxidizing metal oxide. It is believed that yield may be optimized by setting the flow rate in conjunction with a selected reaction temperature that does not result in over-oxidation to achieve maximal oxidation of the alcohol to the aldehyde and minimal formation of acid. Suitable carrier gases for the reaction include nitrogen, argon, helium, neon, xenon, and the like. The preferred carrier gases are nitrogen and helium, and the most preferred carrier gas is nitrogen. Preferably, the oxygen content in the carrier gas is minimized to avoid over-oxidation. The reaction is conducted at a temperature and for a time sufficient to provide the desired 3,3-dimethylbutyraldehyde. Suitable reaction times will vary depending on the conditions, and are typically in the range from about 2 minutes to about 8 hours. Preferable reaction times are from about 2 minutes to about 3 hours, most preferably from about 2 minutes to about 30 minutes.

Any oxidizing metal oxide compound will be suitable for use in this reaction. Such compounds include copper(II) oxide, vanadium pentoxide, manganese dioxide, nickel(IV) oxide, chromium trioxide, and ruthenium dioxide. Preferred metal oxides are copper(II) oxide and manganese dioxide. The most preferred metal oxide is copper(II) oxide. After reaction, it may be possible to regenerate the spent metal oxide by exposure to oxygen at an elevated temperature, e.g., 500° C.

Isolation of the product from this reaction is particularly simple and efficient. The oxidized product, formed in the vapor phase, may be merely condensed from the carrier gas by cooling to form a liquid product of high purity.

In a second embodiment of this invention, oxidation of 3,3-dimethylbutanol to 3,3-dimethylbutyraldehyde is carried out by treating the starting material with 2,2,6,6-tetramethyl-1-piperidinyloxy, free radical (available from Aldrich Chemical Company, Milwaukee, Wis., under the trade name TEMPO) and an oxidizing agent in a solvent. The TEMPO is generally present in a molar ratio to the 3,3-dimethylbutanol in a range from about 0.5:100 to about 2:100, preferably about 0.75:100 to about 1:100.

Suitable oxidizing agents include sodium hypochlorite, calcium hypochlorite, potassium hypochlorite, lithium hypochlorite, hydrogen peroxide, and peracetic acid. The most preferred oxidizing agent is sodium hypochlorite. Preferably, the molar ratio of oxidizing agent to 3,3-dimethylbutanol is in the range from about 0.5:1 to about 10:1, and most preferably from about 1:1 to about 2:1.

This reaction is conducted for a time and at a temperature sufficient to provide for the formation of 3,3-dimethylbutyraldehyde. Suitable reaction temperatures for this embodiment are typically in the range from about −10° C. to about 15° C., preferably from about −5° C. to about 15° C., most preferably from 5° C to 15° C. Reaction times will vary considerably depending on the exact configuration of the equipment used.

Suitable solvents for this embodiment of the invention include all those which dissolve the reactants and which are not susceptible to oxidation by the reagents employed in the reaction. Such solvents include heptane, toluene, ethyl acetate, dichloromethane, and water. The preferred solvents are dichloromethane, toluene and heptane, and the most preferred solvent is dichloromethane. The oxidizing agent is typically added as an aqueous solution to a solution of the starting material and TEMPO in the solvent. Addition of about 0.1 equivalents of potassium bromide to the reaction mixture reduces reaction times. Without being bound to theory, the KBr is believed to enhance reaction speed as the result of the formation of the more powerful oxidant HOBr.

The 3,3-dimethylbutyraldehyde produced by the oxidation method of this invention is useful as an intermediate in the preparation of the sweetener N-N-(3,3-dimethylbutyl)-L-α-aspartyl-L-phenylalanine.

The examples which follow are intended as an illustration of certain preferred embodiments of the invention and no limitation of the invention is implied.

EXAMPLE 1

Oxidation of 3,3-Dimethylbutanol by Copper(II) Oxide

Vapors of 3,3-Dimethylbutanol were passed along with a flow of nitrogen gas at 30 ml/min. through a stainless steel column (6'×¼") packed with copper oxide wire worm (available from Aldrich Chemical Co., Milwaukee, Wis.) and plugged at each end with glass wool in a gas chromatograph. The injector and detector temperatures were set at 200° C. When the column temperature was set at 250° C. a mixture of 70% 3,3-dimethylbutyraldehyde was obtained and 30% of the starting alcohol along with a negligible amount of acid. At a column temperature of 300° C, almost complete oxidation of the alcohol occurred, but approximately 30% of acid was formed along with the 3,3-dimethylbutyraldehyde. The formation of 3,3-dimethylbutyraldehyde was confirmed by capillary GC analysis.

EXAMPLE 2

Oxidation of 3,3-Dimethylbutanol by Sodium Hypochlorite Catalyzed with TEMPO

To a mixture of 3,3-dimethyl-1-butanol (51.09 g, 0.5 mol) and 2,2,6,6-tetramethylpiperidin-1-oxyl (TEMPO, 0.78 g, 5 mmol) in dichloromethane (150 ml) was added a solution of potassium bromide (5.95 g, 0.05 mol) in water (25 ml). The mixture was cooled to −5° C. to 0° C. and then aqueous sodium hypochlorite (550 ml, 1M, 0.55 mol) was added to it over a period of 15–25 minutes while maintaining the pH at 9.5 and the temperature between 5° C. and 15° C. The reaction mixture was stirred for another 15 minutes. The organic layer was separated and the aqueous phase was extracted with dichloromethane (100 ml) containing potassium iodide (1.6 g, 0.01 mol) to remove the TEMPO. The combined organic layer was washed with 10% hydrochloric acid (100 ml) and then with 10% aqueous sodium thiosulfate (50 ml) and water (50 ml). The organic layer was dried over anhydrous magnesium sulfate, filtered and distilled at atmospheric pressure to give 40 g (80%) of 3,3-dimethylbutyraldehyde as a colorless oil. Advantageously, no rearrangement of the t-butyl group of the hindered alcohol, i.e., 3,3-dimethylbutanol, to pinacol was found under those conditions.

Other variations and modifications of this invention will be obvious to those skilled in the art. This invention is not limited except as set forth in the claims.

What is claimed is:

1. A method for preparing 3,3-dimethylbutyraldehyde comprising the step of contacting 3,3-dimethylbutanol with an oxidizing component selected from the group consisting of:

(i) an oxidizing metal oxide; or (ii) a 2,2,6,6-tetramethyl-1-piperidinyloxy, free radical and an oxidizing agent, at a temperature sufficient to form said 3,3-dimethylbutyraldehyde.

2. The method of claim 1, wherein the oxidizing component is an oxidizing metal oxide.

3. The method of claim 2 wherein the oxidizing metal oxide is copper(II) oxide.

4. The method of claim 1, wherein the oxidizing component is 2,2,6,6-tetramethyl-1-piperidinyloxy, free radical and an oxidizing agent.

5. The method of claim 4, wherein the oxidizing agent is sodium hypochlorite.

6. A method for preparing 3,3-dimethylbutyraldehyde comprising the step of contacting 3,3-dimethylbutanol in a vapor phase with an oxidizing metal oxide at a temperature sufficient to form said 3,3-dimethylbutyraldehyde.

7. The method of claim 6, wherein the oxidizing metal oxide is copper(II) oxide.

8. The method of claim 7, wherein the temperature is from about 250° C. to about 350° C.

9. The method of claim 8, wherein the vapor phase comprises 3,3-dimethylbutanol and a carrier gas.

10. The method of claim 9, wherein the carrier gas is selected from the group consisting of nitrogen, argon, helium, neon and xenon.

11. The method of claim 10, wherein the time is from about 2 minutes to about 8 hours.

12. A method for preparing 3,3-dimethylbutyraldehyde comprising the step of treating 3,3-dimethylbutanol with 2,2,6,6-tetramethyl-1-piperidinyloxy, free radical and an oxidizing agent in a solvent at a temperature ranging from −10° to 15° C. to form said 3,3-dimethylbutyraldehyde.

13. The method of claim 12, wherein the oxidizing agent is sodium hypochlorite.

14. The method of claim 13, wherein the sodium hypochlorite and the 3,3-dimethylbutanol are reacted in a molar ratio of from about 0.5:1 to about 10:1.

15. The method of claim 14, wherein the 2,2,6,6-tetramethyl-1-piperidinyloxy, free radical and the 3,3-dimethylbutanol are reacted in a molar ratio of from about 0.5:100 to about 2:100.

16. The method of claim 15, wherein the solvent is selected from the group consisting of heptane, toluene, ethyl acetate, and dichloromethane.

17. The method of claim 16, wherein potassium bromide is added to the solvent in an amount effective to reduce the time of reaction.

* * * * *